US008709482B2

(12) United States Patent
Robertson

(10) Patent No.: US 8,709,482 B2
(45) Date of Patent: *Apr. 29, 2014

(54) STABILISED PROSTAGLANDIN COMPOSITION

(71) Applicant: Ferring B.V., Hoofddorp (NL)

(72) Inventor: Steven Robertson, Motherwell (GB)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/906,905

(22) Filed: May 31, 2013

(65) Prior Publication Data

US 2013/0261179 A1  Oct. 3, 2013

Related U.S. Application Data

(63) Continuation of application No. 11/573,256, filed as application No. PCT/GB2005/002951 on Jul. 28, 2005, now Pat. No. 8,491,934.

(51) Int. Cl.
*A61K 9/14* (2006.01)

(52) U.S. Cl.
USPC ........................................................ 424/486

(58) Field of Classification Search
None
See application file for complete search history.

(56) References Cited

U.S. PATENT DOCUMENTS

| | | |
|---|---|---|
| 3,487,068 A | 12/1969 | Morozowich et al. |
| 3,565,991 A | 2/1971 | Short |
| 3,598,122 A | 8/1971 | Zaffaroni |
| 3,598,123 A | 8/1971 | Zaffaroni |
| 3,639,157 A | 2/1972 | Wunder et al. |
| 3,731,683 A | 5/1973 | Zaffaroni |
| 3,734,097 A | 5/1973 | Zaffaroni |
| 3,737,521 A | 6/1973 | Born |
| 3,760,805 A | 9/1973 | Higuchi |
| 3,797,494 A | 3/1974 | Zaffaroni |
| 3,830,907 A | 8/1974 | Short |
| 3,845,761 A | 11/1974 | Zaffaroni |
| 3,845,770 A | 11/1974 | Theeuwes et al. |
| 3,854,480 A | 12/1974 | Zaffaroni |
| 3,860,701 A | 1/1975 | Short |
| 3,867,933 A | 2/1975 | Kitrilakis |
| 3,881,043 A | 4/1975 | Rieser et al. |
| 3,892,842 A | 7/1975 | Zaffaroni |
| 3,896,819 A | 7/1975 | Zaffaroni et al. |
| 3,901,852 A | 8/1975 | Shah |
| 3,916,898 A | 11/1975 | Robinson |
| 3,916,899 A | 11/1975 | Theeuwes et al. |

(Continued)

FOREIGN PATENT DOCUMENTS

| | | |
|---|---|---|
| DE | 19842636 A1 | 3/1999 |
| DE | 19742217 A1 | 4/1999 |

(Continued)

OTHER PUBLICATIONS

Abraham, et al., "Bioresorbable poly(ester-ether urethane)s from L-lysine diisocyanate and triblock copolymers with different hydrophilic character." Journal of Biomedical Materials Research Part A (2006) 76(4): 729-736.

(Continued)

*Primary Examiner* — Paul Dickinson

(74) *Attorney, Agent, or Firm* — Fish & Richardson P.C.

(57) ABSTRACT

A pharmaceutical delivery device, such as a suppository or pessary, comprises a synthetic prostaglandin $PGE_1$ analogue (e.g. misoprostol) in a solid polyurethane hydrogel.

21 Claims, 2 Drawing Sheets

(56) References Cited

U.S. PATENT DOCUMENTS

Figure 1:
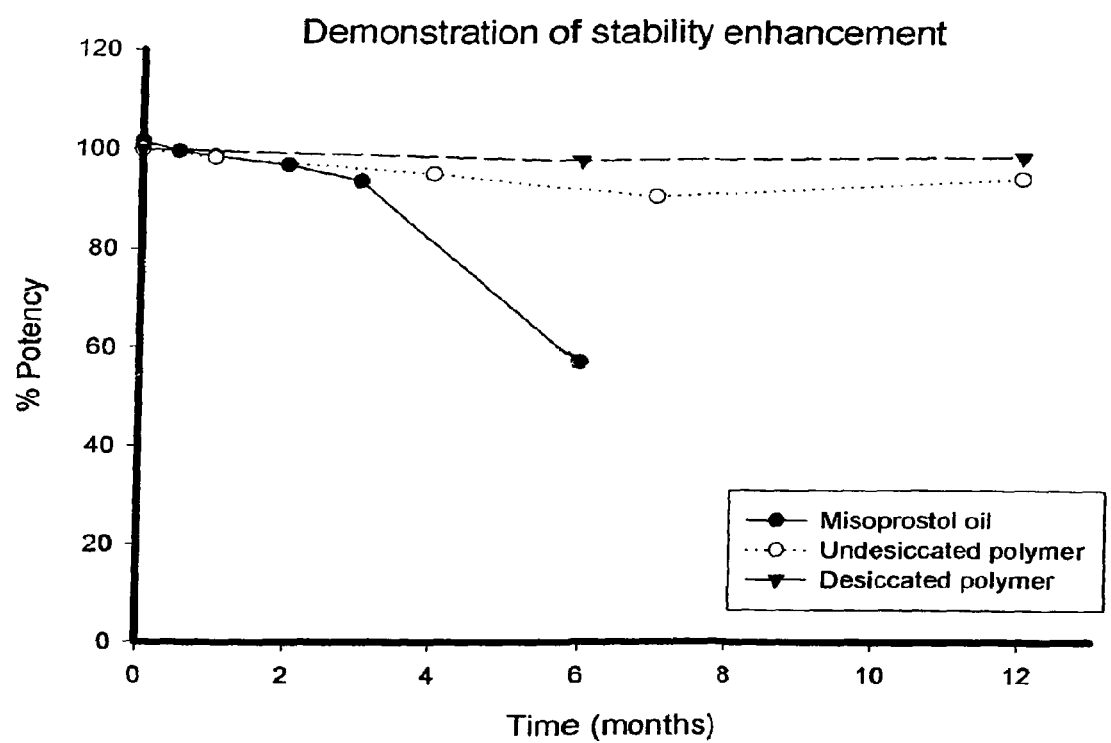

| | | |
|---|---|---|
| 3,921,636 A | 11/1975 | Zaffaroni |
| 3,931,113 A | 1/1976 | Seeger et al. |
| 3,934,580 A | 1/1976 | Cournut |
| 3,941,880 A | 3/1976 | Short |
| 3,948,254 A | 4/1976 | Zaffaroni |
| 3,948,262 A | 4/1976 | Zaffaroni |
| 3,967,618 A | 7/1976 | Zaffaroni |
| 3,993,072 A | 11/1976 | Zaffaroni |
| 3,993,073 A | 11/1976 | Zaffaroni |
| 3,995,631 A | 12/1976 | Higuchi et al. |
| 4,018,918 A | 4/1977 | Ayer et al. |
| 4,034,756 A | 7/1977 | Higuchi et al. |
| 4,036,227 A | 7/1977 | Zaffaroni et al. |
| 4,036,360 A | 7/1977 | Deffeyes |
| 4,041,208 A | 8/1977 | Seeger et al. |
| 4,093,708 A | 6/1978 | Zaffaroni et al. |
| 4,096,238 A | 6/1978 | Zaffaroni et al. |
| 4,098,747 A | 7/1978 | Bailey et al. |
| 4,135,514 A | 1/1979 | Zaffaroni et al. |
| 4,142,526 A | 3/1979 | Zaffaroni et al. |
| 4,202,880 A | 5/1980 | Fildes et al. |
| 4,205,115 A | 5/1980 | Piccirilli et al. |
| 4,215,691 A | 8/1980 | Wong |
| 4,235,988 A | 11/1980 | Fildes et al. |
| 4,237,885 A | 12/1980 | Wong et al. |
| 4,250,611 A | 2/1981 | Wong |
| 4,264,757 A | 4/1981 | Park |
| 4,276,405 A | 6/1981 | Koleske et al. |
| 4,286,587 A | 9/1981 | Wong |
| 4,289,757 A | 9/1981 | Glenn |
| 4,327,727 A | 5/1982 | Prahl et al. |
| 4,379,915 A | 4/1983 | Watanabe et al. |
| 4,402,695 A | 9/1983 | Wong |
| 4,404,296 A | 9/1983 | Schapel |
| 4,426,485 A | 1/1984 | Hoy et al. |
| 4,438,225 A | 3/1984 | Peerman |
| 4,447,591 A | 5/1984 | Watanabe et al. |
| 4,466,936 A | 8/1984 | Schapel |
| 4,503,216 A | 3/1985 | Fagerburg et al. |
| 4,568,741 A | 2/1986 | Livingston |
| 4,594,240 A | 6/1986 | Kawata et al. |
| 4,596,576 A | 6/1986 | de Nijs |
| 4,647,596 A | 3/1987 | Ishii et al. |
| 4,694,238 A | 9/1987 | Norton |
| 4,707,495 A | 11/1987 | Rosenthale et al. |
| 4,731,289 A | 3/1988 | Coleman |
| 4,767,787 A | 8/1988 | Kawata et al. |
| 4,804,691 A | 2/1989 | English et al. |
| 4,814,182 A | 3/1989 | Graham et al. |
| 4,818,517 A | 4/1989 | Kwee et al. |
| 4,894,238 A | 1/1990 | Embry et al. |
| 4,895,934 A | 1/1990 | Matier et al. |
| 4,917,686 A | 4/1990 | Bayston et al. |
| 4,931,288 A | 6/1990 | Embrey et al. |
| 4,933,418 A | 6/1990 | Sterrett |
| 4,940,588 A | 7/1990 | Sparks et al. |
| 4,945,149 A | 7/1990 | Matsumoto et al. |
| 4,952,402 A | 8/1990 | Sparks et al. |
| 4,954,043 A | 9/1990 | Yoshida et al. |
| 4,973,304 A | 11/1990 | Graham et al. |
| 5,000,955 A | 3/1991 | Gould et al. |
| 5,002,540 A | 3/1991 | Brodman et al. |
| 5,017,382 A | 5/1991 | Embrey et al. |
| 5,023,252 A | 6/1991 | Hseih |
| 5,035,891 A | 7/1991 | Runkel et al. |
| 5,045,622 A | 9/1991 | Kohno et al. |
| 5,049,638 A | 9/1991 | Matsumoto et al. |
| 5,055,516 A | 10/1991 | Fisch et al. |
| 5,057,573 A | 10/1991 | Pascault et al. |
| 5,061,254 A | 10/1991 | Karakelle et al. |
| 5,079,009 A | 1/1992 | Embrey et al. |
| 5,100,926 A | 3/1992 | Kondo et al. |
| 5,110,598 A | 5/1992 | Kwan et al. |
| 5,114,718 A | 5/1992 | Damani |
| 5,116,932 A | 5/1992 | Fujiwa |
| 5,118,779 A | 6/1992 | Szycher |
| 5,130,126 A | 7/1992 | Koyama et al. |
| 5,134,151 A | 7/1992 | Bartroli et al. |
| 5,156,900 A | 10/1992 | Nishimura |
| 5,159,047 A | 10/1992 | Simms |
| 5,176,907 A | 1/1993 | Leong |
| 5,178,874 A | 1/1993 | Kwan et al. |
| 5,219,663 A | 6/1993 | Kohno et al. |
| 5,219,885 A | 6/1993 | Frolich et al. |
| 5,252,602 A | 10/1993 | Alam et al. |
| 5,269,321 A | 12/1993 | MacDonald et al. |
| 5,283,297 A | 2/1994 | Miyachi et al. |
| 5,310,759 A | 5/1994 | Bockman |
| 5,312,865 A | 5/1994 | Hoefer et al. |
| 5,322,063 A | 6/1994 | Allen et al. |
| 5,324,746 A | 6/1994 | McKee et al. |
| 5,326,632 A | 7/1994 | Zenda et al. |
| 5,328,954 A | 7/1994 | Sarangapani |
| 5,354,556 A | 10/1994 | Sparks et al. |
| 5,374,704 A | 12/1994 | Muller et al. |
| 5,464,868 A | 11/1995 | Frolich et al. |
| 5,470,829 A | 11/1995 | Prisell et al. |
| 5,472,785 A | 12/1995 | Stobbie et al. |
| 5,474,767 A | 12/1995 | Tremont |
| 5,505,962 A | 4/1996 | Sparks |
| 5,510,384 A | 4/1996 | McKee et al. |
| 5,514,698 A | 5/1996 | Ahmad et al. |
| 5,527,534 A | 6/1996 | Myhling |
| 5,574,102 A | 11/1996 | Tanigami et al. |
| 5,578,640 A | 11/1996 | Hanson |
| 5,578,643 A | 11/1996 | Hanson |
| 5,605,931 A | 2/1997 | Hanson |
| 5,627,254 A | 5/1997 | Oriani |
| 5,634,895 A | 6/1997 | Igo et al. |
| 5,650,171 A | 7/1997 | Quigley et al. |
| 5,652,274 A | 7/1997 | Martin |
| 5,659,003 A | 8/1997 | Menovcik et al. |
| 5,676,939 A | 10/1997 | Tremont |
| 5,681,278 A | 10/1997 | Igo et al. |
| 5,681,850 A | 10/1997 | Frolich et al. |
| 5,686,425 A | 11/1997 | Lee |
| 5,693,319 A | 12/1997 | Tremont |
| 5,700,483 A | 12/1997 | Quigley et al. |
| 5,710,215 A | 1/1998 | Abend |
| 5,716,676 A | 2/1998 | Schutze et al. |
| 5,723,552 A | 3/1998 | Menovcik et al. |
| 5,726,244 A | 3/1998 | McGee et al. |
| 5,726,274 A | 3/1998 | Menovcik et al. |
| 5,731,303 A | 3/1998 | Hsieh |
| 5,733,538 A | 3/1998 | Riffle |
| 5,739,113 A | 4/1998 | Lee |
| 5,744,550 A | 4/1998 | Menovcik et al. |
| 5,747,058 A | 5/1998 | Tipton et al. |
| 5,747,582 A | 5/1998 | Schutze et al. |
| 5,760,127 A | 6/1998 | Bammel et al. |
| 5,763,399 A | 6/1998 | Lee |
| 5,770,650 A | 6/1998 | McGee et al. |
| 5,777,048 A | 7/1998 | Ohrbom et al. |
| 5,780,049 A | 7/1998 | Deckner et al. |
| 5,792,810 A | 8/1998 | Menovcik et al. |
| 5,795,567 A | 8/1998 | Tremont |
| 5,817,343 A | 10/1998 | Burke |
| 5,827,925 A | 10/1998 | Tremont et al. |
| 5,827,930 A | 10/1998 | Ohrbom et al. |
| 5,827,931 A | 10/1998 | Menovcik et al. |
| 5,843,961 A | 12/1998 | Kock et al. |
| 5,849,803 A | 12/1998 | Kock et al. |
| 5,853,767 A | 12/1998 | Melman |
| 5,854,385 A | 12/1998 | McGee et al. |
| 5,855,906 A | 1/1999 | McClay |
| 5,872,195 A | 2/1999 | Green et al. |
| 5,877,216 A | 3/1999 | Place et al. |
| 5,886,039 A | 3/1999 | Kock et al. |
| 5,888,930 A | 3/1999 | Smith et al. |
| 5,891,915 A | 4/1999 | Wysor et al. |
| 5,897,879 A | 4/1999 | Friedman et al. |
| 5,900,433 A | 5/1999 | Igo et al. |
| 5,935,939 A | 8/1999 | Kararli et al. |
| 5,942,512 A | 8/1999 | Kock et al. |

(56) References Cited

U.S. PATENT DOCUMENTS

| | | |
|---|---|---|
| 5,942,545 A | 8/1999 | Samour et al. |
| 5,948,416 A | 9/1999 | Wagner et al. |
| 5,959,775 A | 9/1999 | Joseph et al. |
| 5,965,662 A | 10/1999 | Krebs et al. |
| 5,968,542 A | 10/1999 | Tipton |
| 5,972,372 A | 10/1999 | Saleh et al. |
| 5,973,002 A | 10/1999 | Frolich et al. |
| 5,977,172 A | 11/1999 | Yoshikawa et al. |
| 5,985,859 A | 11/1999 | Luo |
| 5,994,479 A | 11/1999 | Green et al. |
| 5,994,492 A | 11/1999 | Graham et al. |
| 6,008,312 A | 12/1999 | Shirasaka |
| 6,013,637 A | 1/2000 | Klein et al. |
| 6,022,554 A | 2/2000 | Lee et al. |
| 6,028,057 A | 2/2000 | Burns |
| 6,031,002 A | 2/2000 | Wysor et al. |
| 6,039,968 A | 3/2000 | Nabahi |
| 6,040,062 A | 3/2000 | McGee et al. |
| 6,043,224 A | 3/2000 | Lee et al. |
| 6,046,244 A | 4/2000 | Buyuktimkin et al. |
| 6,080,825 A | 6/2000 | Ohrbom et al. |
| 6,084,038 A | 7/2000 | Ohrbom et al. |
| 6,086,909 A | 7/2000 | Harrison et al. |
| 6,093,270 A | 7/2000 | Ferencz et al. |
| 6,103,256 A | 8/2000 | Nabahi |
| 6,103,765 A | 8/2000 | Neal |
| 6,103,852 A | 8/2000 | Shirasaka |
| 6,114,444 A | 9/2000 | Rehfuss et al. |
| 6,117,024 A | 9/2000 | Dewanjee |
| 6,117,843 A | 9/2000 | Baroody et al. |
| 6,123,963 A | 9/2000 | Kim et al. |
| 6,126,958 A | 10/2000 | Saleh et al. |
| 6,130,200 A | 10/2000 | Brodbeck et al. |
| 6,130,309 A | 10/2000 | Reich et al. |
| 6,140,453 A | 10/2000 | Julia et al. |
| 6,150,489 A | 11/2000 | Pudleiner et al. |
| 6,160,058 A | 12/2000 | Ohrbom et al. |
| 6,184,248 B1 | 2/2001 | Lee et al. |
| 6,187,756 B1 | 2/2001 | Lee et al. |
| 6,188,039 B1 | 2/2001 | Gass |
| 6,197,327 B1 | 3/2001 | Harrison et al. |
| 6,210,343 B1 | 4/2001 | Kanakaris et al. |
| 6,210,441 B1 | 4/2001 | Flodin |
| 6,221,997 B1 | 4/2001 | Woodhouse et al. |
| 6,284,836 B1 | 9/2001 | Hassel et al. |
| 6,294,550 B1 | 9/2001 | Place et al. |
| 6,303,147 B1 | 10/2001 | Gilis |
| 6,303,606 B1 | 10/2001 | Leonardi et al. |
| 6,306,841 B1 | 10/2001 | Place et al. |
| 6,323,241 B1 | 11/2001 | Yeager et al. |
| 6,328,991 B1 | 12/2001 | Myhling |
| 6,335,003 B1 | 1/2002 | Kim et al. |
| 6,346,599 B1 | 2/2002 | Goldberg et al. |
| 6,359,100 B1 | 3/2002 | Hostettler et al. |
| 6,403,665 B1 | 6/2002 | Sieker et al. |
| 6,410,595 B1 | 6/2002 | Neal |
| 6,413,536 B1 | 7/2002 | Gibson et al. |
| 6,414,027 B1 | 7/2002 | Neal |
| 6,414,028 B1 | 7/2002 | Büyüktimkin et al. |
| 6,416,779 B1 | 7/2002 | D Augustine et al. |
| 6,420,510 B1 | 7/2002 | Kaufhold et al. |
| 6,423,788 B1 | 7/2002 | Bammel et al. |
| 6,440,568 B1 | 8/2002 | Kayanoki et al. |
| 6,469,016 B1 | 10/2002 | Place et al. |
| 6,469,055 B2 | 10/2002 | Lee et al. |
| 6,471,955 B1 | 10/2002 | Tremont et al. |
| 6,472,434 B1 | 10/2002 | Place et al. |
| 6,482,345 B1 | 11/2002 | Dewanjee |
| 6,486,207 B2 | 11/2002 | Yeager et al. |
| 6,488,953 B2 | 12/2002 | Halliday et al. |
| 6,495,157 B1 | 12/2002 | Pena et al. |
| 6,511,388 B1 | 1/2003 | Dewanjee |
| 6,512,073 B2 | 1/2003 | Gertzmann et al. |
| 6,521,164 B1 | 2/2003 | Plummer et al. |
| 6,537,970 B1 | 3/2003 | Vulpescu et al. |
| 6,543,828 B1 | 4/2003 | Gass |
| 6,545,119 B2 | 4/2003 | Kizumoto et al. |
| 6,559,184 B2 | 5/2003 | Neal |
| 6,572,874 B1 | 6/2003 | Harrison et al. |
| 6,586,553 B1 | 7/2003 | Mühlfeld et al. |
| 6,589,990 B1 | 7/2003 | Kanakaris et al. |
| 6,592,472 B2 | 7/2003 | Dewanjee |
| 6,593,313 B2 | 7/2003 | Place et al. |
| 6,593,369 B2 | 7/2003 | Neal |
| 6,607,686 B2 | 8/2003 | Dewanjee |
| 6,630,050 B1 | 10/2003 | Moeller et al. |
| 6,632,913 B2 | 10/2003 | Matsumoto et al. |
| 6,641,064 B1 | 11/2003 | Dentler et al. |
| 6,642,274 B1 | 11/2003 | Neal |
| 6,664,290 B1 | 12/2003 | El-Rafaey |
| 6,693,135 B2 | 2/2004 | Yeager et al. |
| 6,740,333 B2 | 5/2004 | Beckett et al. |
| 6,790,926 B1 | 9/2004 | Spijkers et al. |
| 6,794,372 B2 | 9/2004 | Del Soldato et al. |
| 6,825,234 B2 | 11/2004 | Yeager et al. |
| 6,841,574 B1 | 1/2005 | Mo et al. |
| 6,861,503 B2 | 3/2005 | Shalaby |
| 6,953,800 B2 | 10/2005 | Leonardi et al. |
| 6,992,161 B1 | 1/2006 | Kim et al. |
| 7,053,209 B1 | 5/2006 | Gibson et al. |
| 7,179,481 B2 | 2/2007 | Villanueva |
| 7,485,666 B2 | 2/2009 | Villanueva et al. |
| 7,670,606 B2 | 3/2010 | Volkmann |
| 7,717,892 B2 | 5/2010 | Bartning et al. |
| 7,795,467 B1 | 9/2010 | Pacetti et al. |
| 7,829,112 B2 | 11/2010 | Ron et al. |
| 7,833,543 B2 | 11/2010 | Gibson et al. |
| 7,833,545 B2 | 11/2010 | Ron et al. |
| 7,838,024 B2 | 11/2010 | Ron et al. |
| 7,883,718 B2 | 2/2011 | Ron et al. |
| 7,892,163 B2 | 2/2011 | Bartning et al. |
| 2001/0014715 A1 | 8/2001 | Blum et al. |
| 2001/0044467 A1 | 11/2001 | Neal |
| 2001/0051656 A1 | 12/2001 | Place et al. |
| 2001/0051694 A1 | 12/2001 | Julia et al. |
| 2002/0004529 A1 | 1/2002 | Neal |
| 2002/0013304 A1 | 1/2002 | Wilson et al. |
| 2002/0028846 A1 | 3/2002 | Yeager et al. |
| 2002/0037491 A1 | 3/2002 | Halliday et al. |
| 2002/0039935 A1 | 4/2002 | Dewanjee |
| 2002/0045665 A1 | 4/2002 | Yeager et al. |
| 2002/0052407 A1 | 5/2002 | Lee et al. |
| 2002/0062097 A1 | 5/2002 | Simpson |
| 2002/0077442 A1 | 6/2002 | Gertzmann et al. |
| 2002/0077444 A1 | 6/2002 | Matsumoto et al. |
| 2002/0099003 A1 | 7/2002 | Wilson et al. |
| 2002/0115814 A1 | 8/2002 | Woodhouse et al. |
| 2002/0115976 A1 | 8/2002 | Fleming |
| 2002/0119833 A1 | 8/2002 | Dewanjee |
| 2002/0128314 A1 | 9/2002 | Neal |
| 2002/0132965 A1 | 9/2002 | Gertzmann et al. |
| 2002/0161009 A1 | 10/2002 | Leonardi et al. |
| 2003/0022022 A1 | 1/2003 | Kizumoto et al. |
| 2003/0032754 A1 | 2/2003 | Kaufhold et al. |
| 2003/0032759 A1 | 2/2003 | Fischer et al. |
| 2003/0045668 A1 | 3/2003 | Fischer et al. |
| 2003/0060589 A1 | 3/2003 | Shimizu et al. |
| 2003/0122282 A1 | 7/2003 | Plummer et al. |
| 2003/0129241 A1 | 7/2003 | Yeager et al. |
| 2003/0134903 A1 | 7/2003 | Yeager et al. |
| 2003/0144454 A1 | 7/2003 | Krebs et al. |
| 2003/0158369 A1 | 8/2003 | Slagel |
| 2003/0207852 A1 | 11/2003 | Place et al. |
| 2003/0212139 A1 | 11/2003 | Neal |
| 2004/0014761 A1 | 1/2004 | Place et al. |
| 2004/0044080 A1 | 3/2004 | Place et al. |
| 2004/0047910 A1 | 3/2004 | Beckett et al. |
| 2004/0110843 A1 | 6/2004 | Yeager et al. |
| 2004/0115229 A1 | 6/2004 | Roby |
| 2004/0131664 A1 | 7/2004 | Mo et al. |
| 2004/0142847 A1 | 7/2004 | Bayersdoerfer et al. |
| 2004/0157766 A1 | 8/2004 | Embil et al. |
| 2004/0265355 A1 | 12/2004 | Shalaby |
| 2004/0266688 A1 | 12/2004 | Nayak |

(56) References Cited

U.S. PATENT DOCUMENTS

| | | | |
|---|---|---|---|
| 2005/0004226 A1 | 1/2005 | Lu et al. |
| 2005/0013793 A1 | 1/2005 | Beckman et al. |
| 2005/0031690 A1 | 2/2005 | Rohrs et al. |
| 2005/0048104 A1 | 3/2005 | Venkatraman et al. |
| 2005/0053639 A1 | 3/2005 | Shalaby |
| 2005/0053670 A1 | 3/2005 | Schaub |
| 2005/0070516 A1 | 3/2005 | Wilson et al. |
| 2005/0090474 A1 | 4/2005 | Naor |
| 2005/0095245 A1 | 5/2005 | Riley et al. |
| 2005/0161030 A1 | 7/2005 | Roberts et al. |
| 2005/0169975 A1 | 8/2005 | Suzuki et al. |
| 2005/0181030 A1 | 8/2005 | Mo et al. |
| 2005/0187342 A1 | 8/2005 | Schieferstein et al. |
| 2005/0208152 A1 | 9/2005 | Milankovits |
| 2005/0238722 A1 | 10/2005 | Pathak et al. |
| 2005/0245902 A1 | 11/2005 | Cornish et al. |
| 2006/0003950 A1 | 1/2006 | Strugnell et al. |
| 2006/0018951 A1 | 1/2006 | Maniar et al. |
| 2006/0041021 A1 | 2/2006 | Wilson et al. |
| 2006/0052341 A1 | 3/2006 | Cornish et al. |
| 2006/0078616 A1 | 4/2006 | Georgewill et al. |
| 2006/0093675 A1 | 5/2006 | Ebmeier et al. |
| 2006/0134161 A1 | 6/2006 | Halliday et al. |
| 2006/0183724 A1 | 8/2006 | Diliberti et al. |
| 2006/0210599 A1 | 9/2006 | Gibson et al. |
| 2007/0043332 A1 | 2/2007 | Malcolm et al. |
| 2007/0128154 A1 | 6/2007 | Hadba et al. |
| 2007/0135605 A1 | 6/2007 | Hadba et al. |
| 2007/0148105 A1 | 6/2007 | Spector |
| 2007/0155906 A1 | 7/2007 | Hissink et al. |
| 2007/0166382 A1 | 7/2007 | Kiser et al. |
| 2007/0282093 A1 | 12/2007 | Yoshimura et al. |
| 2008/0009663 A1 | 1/2008 | Bartning et al. |
| 2008/0009666 A1 | 1/2008 | Bartning et al. |
| 2008/0108775 A1 | 5/2008 | Schieferstein et al. |
| 2008/0140185 A1 | 6/2008 | Kiser et al. |
| 2008/0145419 A1 | 6/2008 | Gibson et al. |
| 2008/0152708 A1 | 6/2008 | Gibson et al. |
| 2008/0199511 A1 | 8/2008 | Sitruk-Ware et al. |
| 2008/0206310 A1 | 8/2008 | Davis |
| 2008/0207571 A1 | 8/2008 | Davis |
| 2008/0262613 A1 | 10/2008 | Gogolewski |
| 2008/0271190 A1 | 10/2008 | Holland |
| 2008/0286339 A1 | 11/2008 | Ron et al. |
| 2009/0004246 A1 | 1/2009 | Woolfson et al. |
| 2009/0011209 A1 | 1/2009 | Steinberger et al. |
| 2009/0060982 A1 | 3/2009 | Ron et al. |
| 2009/0061172 A1 | 3/2009 | Hayashi et al. |
| 2009/0081278 A1 | 3/2009 | De Graaff et al. |
| 2009/0203591 A1 | 8/2009 | Bagchi et al. |
| 2009/0203772 A1 | 8/2009 | Villanueva et al. |
| 2009/0291120 A1 | 11/2009 | Tuominen et al. |
| 2010/0104619 A1 | 4/2010 | De Graaff et al. |
| 2010/0203104 A1 | 8/2010 | De Graaff et al. |
| 2010/0285094 A1 | 11/2010 | Gupta |
| 2011/0045076 A1 | 2/2011 | Kiser et al. |
| 2011/0056501 A1 | 3/2011 | Kortesuo et al. |
| 2011/0059040 A1 | 3/2011 | Kiser et al. |
| 2011/0077578 A1 | 3/2011 | Bartning et al. |
| 2011/0091488 A1 | 4/2011 | Halliday et al. |
| 2011/0150955 A1 | 6/2011 | Klingman |

FOREIGN PATENT DOCUMENTS

| | | |
|---|---|---|
| EP | 335669 A3 | 1/1990 |
| EP | 424164 A2 | 4/1991 |
| EP | 450176 A1 | 10/1991 |
| EP | 401990 A3 | 1/1992 |
| EP | 1063942 A4 | 7/2002 |
| FR | 2557576 B1 | 6/1988 |
| FR | 2705567 A1 | 12/1994 |
| GB | 2047094 A | 11/1980 |
| GB | 2047093 B | 12/1983 |
| GB | 2244920 A | 12/1991 |
| JP | 5600253 A1 | 3/1980 |
| JP | 1135488 C | 2/1983 |
| JP | 1150610 U | 10/1989 |
| JP | 0670952 A1 | 3/1994 |
| JP | 200502691 A1 | 3/2000 |
| JP | 2002515069 A | 5/2002 |
| JP | 2001513550 A5 | 12/2009 |
| JP | 2011507405 A | 3/2011 |
| WO | WO8001984 A1 | 10/1980 |
| WO | WO8905319 A1 | 6/1989 |
| WO | WO8907117 A1 | 8/1989 |
| WO | WO9102763 A1 | 3/1991 |
| WO | WO9403510 A1 | 2/1994 |
| WO | WO9413724 A1 | 6/1994 |
| WO | WO9422934 A1 | 10/1994 |
| WO | WO9606875 A1 | 3/1996 |
| WO | WO9615171 A1 | 5/1996 |
| WO | WO9621427 A1 | 7/1996 |
| WO | WO9631551 A1 | 10/1996 |
| WO | WO9638153 A1 | 12/1996 |
| WO | WO9717386 A1 | 5/1997 |
| WO | WO9724109 A1 | 7/1997 |
| WO | WO9856323 A1 | 12/1998 |
| WO | WO9909964 A2 | 3/1999 |
| WO | WO9947073 A1 | 9/1999 |
| WO | WO9956731 A1 | 9/1999 |
| WO | WO9956731 A1 | 11/1999 |
| WO | WO0000222 A1 | 1/2000 |
| WO | WO0040222 A1 | 7/2000 |
| WO | WO0203896 A1 | 1/2002 |
| WO | WO0209631 A1 | 2/2002 |
| WO | WO03011301 A1 | 2/2003 |
| WO | WO03087183 A1 | 10/2003 |
| WO | WO2004029125 A1 | 4/2004 |
| WO | WO2004084872 A1 | 10/2004 |
| WO | WO2005063145 A1 | 7/2005 |
| WO | WO2005068533 A1 | 7/2005 |
| WO | WO2005089778 A1 | 9/2005 |
| WO | WO2005116100 A1 | 12/2005 |
| WO | WO2006013335 A1 | 2/2006 |
| WO | WO2006048639 A1 | 5/2006 |
| WO | WO2008007098 A2 | 1/2008 |
| WO | WO2009094573 A3 | 10/2009 |
| WO | WO2010035837 A1 | 4/2010 |
| WO | WO2010119029 A1 | 10/2010 |
| WO | WO2011011099 A1 | 1/2011 |
| WO | WO2011039418 A1 | 4/2011 |

OTHER PUBLICATIONS

Australian Office Action dated Feb. 24, 2010, which issued in corresponding Australian Application No. 2005268645.

Australian Office Action dated Aug. 18, 2010, which issued in corresponding Australian Application No. 2005268645.

Baimak et al., "Synthesis and characterization of poly(l-lactide-co-e-caprolactone) copolymers: Effect of stannous octoate initiator and diethylel glycol coinitiator concentration." ScienceAsia 30 (2004):324-334.

Canadian Office Action dated Dec. 1, 2011, which issued in corresponding Canadian Application No. 2575933.

Casteneda, C.S., et al. "Misoprostol Dose Selection in a Controlled-Release Vaginal Insert for Induction of Labor in Nulliparous Women," American Journal of Obstetrics and Gynecology, 193:1071-1075, (Sep. 2005).

Chen, "Stabilization and sustained-release effect of Misoprostol with Methacrylate copolymer", International Journal of Pharmaceutics, 203 (2000) pp. 141-148.

Chinese Office Action mailed Oct. 12, 2010, which issued in corresponding Chinese Application No. 2005800261903.

Chinese Office Action mailed Nov. 13, 2009, which issued in corresponding Chinese Application No. 2005800261903.

Chinese Office Action mailed Apr. 23, 2010, which issued in corresponding Chinese Application No. 2005800261903.

Chinese Office Action mailed May 20, 2010, which issued in corresponding Chinese Application No. 2005800261903.

European Office Action dated Feb. 11, 2010, which issued in corresponding European Application No. 05763115.2.

(56) References Cited

OTHER PUBLICATIONS

European Office Action dated Apr. 7, 2011, which issued in corresponding European Application No. 05763115.2.
Indian Office Action dated Mar. 21, 2012, which issued in corresponding Indian Application No. 697/DELNP/2007.
Japanese Office Action mailed Aug. 16, 2011, which issued in corresponding Japanese Application No. JP2007524389.
Japanese Office Action mailed Jan. 27, 2012, which issued in corresponding Japanese Application No. JP2007524389.
Jianzhong et al. "Polycaprolactone-poly(ethylene glycol) block copolymer III Drug release behavior." Chinese J Polym Sci., 13(2) 1995:154:161.
Kararli, "Stabilization of Misoprostol with Hydroxypropyl Methylcellulose (HMPC) Against Degradation by Water", Pharmaceutical Research, vol. 7, No. 11 (1990).
Lee JW, et al., "Thermoreversible gelation of biodegradable poly(epsilon-caprolactone) and poly(ethylene glycol) multiblock copolymers in aqueous solutions." J Control Release. Jun. 15, 2001; 73(2-3):315-27.
Leiva et al., "Poly(£-caprolactone)-block-poly(ethyleneoxide) - block-poly(£-V caprolactone): Biodegradable triblock copolymer spread at the air-water interface." European Polymer Journal 44(8), Aug. 2008:2589-2598.
Merck Index (Ninth Edition, 1976, p. 4073).
Mexican Office Action mailed Apr. 1, 2011, which issued in corresponding Mexican Application No. MX/a/2007/00115.
New Zealand Examination Report mailed May 1, 2009, which issued in corresponding New Zealand Application No. 552756.
PCT/GB2003/004208 International Search Report dated Jan. 2, 2004.
PCT/GB2005/002951 Written Opinion of the International Searching Authority dated Oct. 6, 2005.
PCT/GB2005/002951 International Preliminary Report on Patentability dated Feb. 6, 2007.
PCT/GB2007/002604, International Search Report, dated Jul. 12, 2007.
PCTGB2007/002604 Written Opinion of International Searching Authority Jul. 12, 2007.
PCT/GB2005/002951 International Search Report dated Oct. 20, 2005.
PCT/GB2007/002401 International Search Report dated Oct. 24, 2007.
PCT/GB2007/002401 Written Opinion of the International Searching Authority dated Oct. 24, 2007.
PCT/GB2007/002415 International Search Report dated Oct. 30, 2007.
PCT/GB2007/002415 Written Opinion of the International Searching Authority dated Oct. 30, 2007.
Santerre, et al., "Understanding the biodegradation of polyurethanes: From classical implants to tissue engineering materials." Biomaterials 26(35), Dec. 2005: 7457-7470.
Sato et al., The effects of a prostaglandin El analogue, misoprostol, on gastric mucosal blood volume index and haemoglobin oxygenation in humans, Journal of Gastroenterology and Hepatology, 2008, 2(6), 499-505.
Tyagi, P., et al., "Sustained Intravesical Drug Delivery Using Thermosensitive Hydrogel," Pharmaceutical Research, 21 (5):832-837 (May 2004).
Yu, J., et al. "Blood interactions with novel polyurethaneurea hydrogels," Biomaterials 12(2): 119-120 (1991).
Zhou et al., "Biodegradable poly(e-caprolactone)-poly(ethylene glycol) block copolymers: characterization and their use as drug carriers for a controlled delivery system." Biomaterials (2003) 24(20): 3563-3570.

STABILISED PROSTAGLANDIN COMPOSITION

CROSS-REFERENCE TO RELATED APPLICATIONS

This application is a continuation application of U.S. application Ser. No. 11/573,256, filed Apr. 19, 2007, which is a National Stage filing under 35 U.S.C. 371 of International Application PCT/GB05/02951, filed Jul. 28, 2005, which claims priority from United Kingdom Patent Application No. 0417401.7, filed Aug. 5, 2004. The contents of all of the prior applications are herein are incorporated by reference.

FIELD OF INVENTION

The present invention provides a pharmaceutical delivery device comprising a synthetic prostaglandin $PGE_1$ analogue, such as misoprostol or analogues or derivatives thereof and a polyurethane hydrogel; and also uses and methods of preparation of such a device.

BACKGROUND OF INVENTION

Prostaglandins are a group of lipids, which are modified fatty acids attached to a 5-membered ring and with biological/pharmaceutical activities suitable for a variety of therapeutic uses. Such uses include reproductive health disorders and disorders linked to inflammatory response. However, prostaglandins are often unstable under ambient conditions and have sometimes proved difficult to store and produce in a form suitable for pharmaceutical/therapeutic use.

A prostaglandin formulation, which allows controlled release of the active compound for therapeutic use is described in patent specifications GB 2047093 and GB 2047094. Such formulations use hydrogels, which are known sustained release delivery vehicles; and in particular, "solid" cross-linked polyurethane materials having the ability to swell and absorb several times their own weight of water whilst retaining their physical integrity. The formulations have been provided as pessaries to deliver dinoprostone (a $PGE_2$ prostaglandin) to the cervix to ripen it prior to the induction of labour, and is available under the trademarks Propess® and Cervidil®. The pessary is enclosed in a net pouch and usually remains in place in the cervix for up to 24 hours. However, this prostaglandin, even when loaded into such hydrogels, is somewhat unstable at room temperature and therefore the pessary is generally stored at temperatures of around −20° C.

Various attempts have been made to provide stabilised formulations of prostaglandins in general. $PGE_2$ prostaglandins tend to be more unstable than $PGE_1$ prostaglandins.

Misoprostol is a synthetic prostaglandin analogue; in particular, a cytoprotective prostaglandin $PGE_1$ analogue. Misoprostol is a compound represented by the following stereoisomeric formulae:

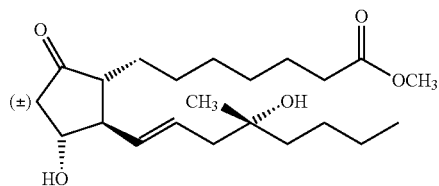

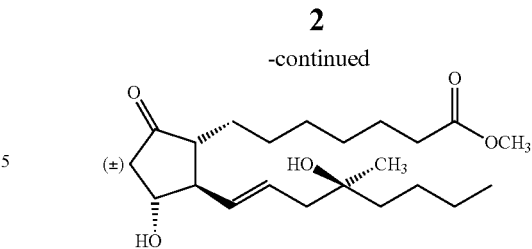

Misoprostol in its physical state is an oil, which is difficult to formulate and unstable at room temperature. Misoprostol possesses mucosal protective properties and is an inhibitor of gastric acid secretion. Misoprostol has been used previously in the treatment and prevention of gastric ulcers, in particular NSAID-induced ulcers.

Misoprostol may be obtained commercially or prepared by known reaction schemes, such as by the methods taught in U.S. Pat. No. 3,965,143, for example.

U.S. Pat. No. 4,301,146 describes a solid state dispersion of misoprostol and polyvinyl pyrrolidone (PVP) or hydroxypropylmethylcellulose (HPMC). These formulations may be in the form of a tablet or capsule.

U.S. Pat. No. 5,935,939 describes a stabilised solid state dispersion of misoprostol and in particular, the preparation of stabilised misoprostol using amorphous or semi-crystalline excipients.

U.S. Pat. No. 6,642,274 discloses use of a large number of prostaglandins, including misoprostol. However, there is no focus on the problems of formulating misoprostol. Hydrogels are mentioned but these are semi-liquid compositions or low melting compositions suitable for suppositories.

US Patent Publication 2003/0050620 discloses prostaglandins in general but not $PGE_1$ analogues. Hydrogels are mentioned but the problems of formulating $PGE_1$ analogues are not addressed.

Other patent publications dealing with prostaglandins and/or hydrogel carriers include U.S. Pat. No. 6,287,588, U.S. Pat. No. 6,589,549, US 2002/0076441, U.S. Pat. No. 6,685,962, US 2003/0021845, US 2003/0049320 and US 2003/0064088.

It is an object of the present invention to provide a $PGE_1$ formulation showing increased stability properties compared with unformulated misoprostol; and in particular to provide a solid state misoprostol formulation which has increased storage stability at room temperature.

SUMMARY OF INVENTION

The present invention is based on the unexpected observation that the stability of a synthetic prostaglandin $PGE_1$ analogue, misoprostol, at room temperature is increased when formulated in a polyurethane hydrogel. This increased stability is surprising and is not exhibited by other prostaglandins, such as dinoprostone, when formulated in this way.

In a first aspect of the present invention there is provided a pharmaceutical delivery device comprising a synthetic prostaglandin $PGE_1$ analogue or derivative thereof in a polyurethane hydrogel.

The pharmaceutical delivery device allows the effective sustained delivery of the pharmaceutical, a synthetic prostaglandin $PGE_1$ analogue, such as misoprostol, from the solid state hydrogel. Typically, the pharmaceutical is intended to be delivered to a patient (human or animal).

Generally, the synthetic prostaglandin $PGE_1$ analogue is dispersed throughout the polyurethane hydrogel matrix.

The polyurethane hydrogel of the pharmaceutical delivery device of the present invention extends to polyurethane hydrogels well known to the man skilled in the art. Without wishing to be bound by theory, said polyurethane hydrogels when hydrated form a gel but do not dissolve. They are solid in the sense that, whilst being swellable, they retain their physical integrity without becoming a liquid or semi-liquid gel. The polyurethane hydrogels are capable of being loaded with the synthetic prostaglandin $PGE_1$ analogue, such as misoprostol. The polyurethane hydrogels may be cross-linked or linear polymers. Furthermore, the polyurethane hydrogels may be swollen in a "wet state" or unswollen in a "dry" or "desiccated" state in the device of the invention. These states will be described further below.

The polyurethane hydrogel used in the delivery device of the present invention may be of the type disclosed in GB 2047093 and GB 2047094. These patent specifications disclose cross-linked polyurethane hydrogels.

Alternatively, the delivery device of the present invention may include a polyurethane hydrogel, as described in patent specification WO 2004/029125. This patent specification discloses linear polyurethane hydrogels. Such linear polyurethane hydrogels may be obtained by reacting a polyethylene glycol and a diol or other difunctional compound with a difunctional isocyanate.

Without wishing to be bound by theory and unless otherwise stated herein, it should be understood that the properties and variables of the hydrogels as described in GB 2047093, GB 2047094 and WO 2004/029125 are applicable to the present invention.

Typically, the cross-linked polyurethane hydrogel (as described in GB 2047093 and GB 2047094) is prepared from a long chain polyethylene glycol (e.g. PEG 2000, 4000, 6000 and 8000, which has been extensively dried), a triol (for example, hexanetriol) as cross-linking agent and a diisocyanate (such as dicyclohexyl methane diisocyanate). The mixture is cured at elevated temperatures in a mould.

Typically, the linear polyurethane hydrogel is prepared from a) a polyethylene oxide, b) a difunctional compound and c) a difunctional isocyanate (as described in WO 2004/029125). Advantageously, the linear polyurethane hydrogel is swellable in water and suitable as a carrier for the synthetic prostaglandin $PGE_1$ analogue in the delivery device of the present invention. Furthermore, the linear polyurethane hydrogel of the delivery device of the present invention may be loaded with poorly water-soluble pharmaceutical agents, such as a synthetic prostaglandin $PGE_1$ analogue, including misoprostol, for example when such agents are dissolved in a common solvent with the polymer. An example of a solvent is ethanol. The resultant solution may then be cast into any desired solid forms.

The polyurethane hydrogels for use in the present invention provide water-swellable polyurethane polymers having swellabilities, for example up to 500%, up to 800% or even about 1,000%. Percent (%) swelling, is understood to mean the increase in weight of the swollen polymer divided by the weight of the dry polymer. Usually, the polymer is swellable in the range 200% to 2000%, for example 250 to 1700%. The linear polyurethane hydrogels are also soluble in certain organic solvents, such as dichloromethane, which allows the hydrogel to be dissolved and cast into films or coatings. Therefore, as mentioned above, it also allows active agents of poor water solubility but which are soluble in organic solvents, such as misoprostol, to be loaded into the polymer.

Polyethylene oxides contain the repeat unit $(CH_2CH_2O)$ and are conveniently prepared by the stepwise addition of ethylene oxide to a compound containing a reactive hydrogen atom. Polyethylene glycols are prepared by the addition of ethylene oxide to ethylene glycol to produce a difunctional polyethylene glycol structure $HO(CH_2CH_2O)_nH$ wherein n is an integer of varying size depending on the molecular weight of polyethylene oxide. For example, polyethylene oxides used in the linear polyurethane hydrogels of the present invention are generally linear polyethylene glycols i.e. diols having a equivalent weight of 1500 to 20,000, particularly 3000 to 10,000 and especially 4000 to 8000. Molecular weights are usually in the region 4000 to 35,000.

In this description the term "equivalent weight" is used as meaning the number average molecular weight divided by the functionality of the compound.

The difunctional compound is reactive with the difunctional isocyanate, and is typically a difunctional amine or diol. Diols in the range $C_5$ to $C_{20}$, preferably $C_8$ to $C_{15}$ are preferred. Thus, decane diol has been found to produce particularly good results. The diol may be a saturated or unsaturated diol. Branched diols may be used but straight chain diols are preferred. The two hydroxy groups are generally on terminal carbon atoms. Thus, preferred diols include 1,6-hexanediol, 1,10-decanediol, 1,12-dodecanediol and 1,16-hexadecanediol.

The difunctional isocyanate is generally one of the conventional diisocyanates, such as dicyclohexylmethane-4,4-diisocyanate, diphenylmethane-4,4-diisocyanate, 1,6-hexamethylene diisocyanate etc.

The ratio of the components (a) to (b) to (c) of the linear polymer described above (in terms of equivalent weights) is generally in the range 0.1-1.5 to 1 to 1.1-2.5, particularly 0.2-0.9 to 1 to 1.2-1.9. A preferred range is 0.5-0.9 to 1 to 1.5-1.9. Of course, the skilled man through reasonable experimentation would determine the best ratio of ingredients to give the desired properties. The amount of component (c) is generally equal to the combined amounts of (a) and (b) to provide the correct stoichiometry.

Linear polyurethane hydrogels produced at extreme ends of the ranges may not necessarily give optimal properties. For example, high amounts of (a) polyethylene oxide may undesirably lead to the polymer being water-soluble. Small amounts may reduce the percentage swelling. Generally, the ratio of (a) polyethylene oxide to (b) difunctional compound is preferable 0.1-1.5 to one, preferably 0.2-0.9 to one.

The linear polyurethane hydrogels are generally produced by melting the previously dried polyethylene glycol together with the difunctional compound (e.g. diol) at a temperature of around 85° C. A catalyst such as ferric chloride is incorporated. The molten mixture is dried under vacuum to remove excess moisture and the diisocyanate added thereto. The reaction mixture is then poured into billet moulds and cured for a specified time. Thus, the linear polyurethane hydrogel is initially formed as a moulded solid. However, the linear polyurethane hydrogels of the delivery device of the present invention are soluble in certain organic solvents. This allows the polymer to be dissolved and the resultant solution cast to form films. The solution may also be employed for coating granules, tablets etc., in order to modify their release properties. Alternatively, the solution can be poured into a non-solvent so as to precipitate polymer/active microparticles.

Generally, the polyurethane hydrogel is washed in water, followed by washing in an ethanol:water mixture before being loaded with a synthetic prostaglandin $PGE_1$ analogue by soaking the hydrogel in an aqueous solution of a synthetic prostaglandin $PGE_1$ analogue of required concentration for a time sufficient for uptake of the synthetic prostaglandin $PGE_1$ analogue to occur, followed by drying the hydrogel down to the required water content. Typically, the synthetic prostaglandin $PGE_1$ analogue is dissolved in organic solvent, such as an ethanol:water solvent, before being loaded into the polyurethane hydrogel.

The term "synthetic prostaglandin $PGE_1$ analogue" as used herein is understood to cover the compound generally known as misoprostol and any analogues or derivatives thereof. Analogues or derivatives thereof are intended to encompass structural analogues or derivatives of the synthetic prostaglandin $PGE_1$ analogue which maintain the essential pharmaceutical activity of the synthetic prostaglandin $PGE_1$ analogue, including misoprostol; for example, prostaglandins of different chain length, or different salts or esters which maintain pharmacological activity. These may also encompass stereoisomers of the synthetic prostaglandin $PGE_1$ analogue, such as misoprostol. It will be understood that the term synthetic prostaglandin $PGE_1$ analogue (or misoprostol) is not intended to encompass naturally occurring $PGE_1$. Synthetic $PGE_1$ analogues or derivatives may be in the form of an ester; such as a methyl ester: whereas said naturally occurring $PGE_1$ is normally in the acid form. One or more $C_{1-6}$ alkyl groups (particularly methyl) may be attached to the prostanoic acid carbon chain, especially at the 15-position. Typically, misoprostol $PGE_1$ analogue or derivative in its physical state is an oil, whereas naturally occurring $PGE_1$ is in a crystalline form.

Misoprostol should be understood to mean $(11\alpha,13E)$-$(\pm)$-11,16-Dihydroxy-16-methyl-9-oxoprost-13-en-1-oic acid methyl ester or analogue(s) or derivative(s) thereof, as described herein. Preferably, misoprostol has the formula $C_{22}H_{33}O_5$ or the general structure as hereinbefore described.

Typically, misoprostol has a molecular weight of around 380.

The delivery device of the present invention may be in the form of a suppository, a pessary for vaginal use, a buccal insert for oral administration, an implant etc. Preferably, the device is in the form of a comfortable unit, which is flexible enough (particularly when swollen) to be accommodated within a body cavity: for example, buccal cavity in intimate contact with the mucosal membrane. Preferred shapes include sheets, discs, ovals, kidney shapes, strips and cylinders. Generally, the smallest dimension is in the range 5-15 mm and the longest dimension in the range 10-25 mm. Preferred thicknesses are in the range 0.5-5 mm, especially 0.5-2.5 mm, particularly 1-2.5 mm and more particularly 0.8-1.5 mm. It will be understood, however, that length and thickness of said delivery device may be altered and designed to preferred sizes per individual patient.

The delivery device of the present invention has a number of applications including the treatment of schizophrenia, prevention of gastric ulcers, mucositis and orthodontic applications. Typically, the device is used for its action upon the female reproductive system of both human and non-human animals. Preferably, the device of the present invention is used in the induction of labour. The device may also be used for first and second trimester abortion and the prevention of postpartum haemorrhage (PPH).

The pharmaceutical delivery device of the present invention is intended to administer a synthetic prostaglandin $PGE_1$ analogue to a patient, remaining in place until partial or complete delivery of the synthetic prostaglandin $PGE_1$ analogue has occurred. The spent delivery device may then be removed from the patient. Advantageously, the delivery device may further comprise means for removal of the device from a patient. For example, using means well known to the person skilled in the art, such as removal means used for conventional tampons for vaginal use.

An objective of the present invention is the stabilisation of a synthetic prostaglandin $PGE_1$ analogue in the delivery device of the present invention, especially at temperature above +4° C., particularly at room temperature of around +20° C. The synthetic prostaglandin $PGE_1$ analogue-containing delivery device of the present invention allows the controlled release of a synthetic prostaglandin $PGE_1$ analogue into a patient. At low water contents, the delivery device may adhere to the mucosal membrane of a patient. The synthetic prostaglandin $PGE_1$ analogue may be absorbed systemically or may exert a local action on adjacent tissue structures. Typical autoadhesive properties for improved means of delivery of said synthetic prostaglandin $PGE_1$ analogue to a patient are described in WO 00/32171.

Typically, stabilisation of synthetic prostaglandin $PGE_1$ analogue is understood to mean the increased stability or, conversely, the decreased degradation of this prostaglandin at temperatures above 4° C. within the delivery device of the present invention. For example, wherein the percent dose of the synthetic prostaglandin $PGE_1$ analogue present within the delivery device of the present invention after storage at temperatures above 4° C. (preferably room temperature of around 20° C.) is within a range of 90-100% of initial dose of the synthetic prostaglandin $PGE_1$ analogue added to the delivery device of the present invention. The stability also depends on the water content of the hydrogel.

If necessary, penetration enhancers, as known in the art, may be employed to assist the rate of transmucosal delivery, depending on the nature of the synthetic prostaglandin $PGE_1$ analogue, for example, its lipophilic or hydrophilic characteristics, size and molecular weight. Generally, the more lipophilic the compound, the better the absorption. The nonionized form of a synthetic prostaglandin $PGE_1$ analogue appears to be best for absorption. In view of the rapid and effective delivery through mucosal tissues, penetration enhancers may not be required. Such penetration enhancers are known from topical application to skin tissue, which constitutes a more significant barrier to absorption. Weak acids and some detergents have been used as penetration enhancers.

The release properties of the polyurethane hydrogel of the delivery device of the present invention may be modified by applying a coating thereto. The synthetic prostaglandin $PGE_1$ analogue may be included in a coating as well as in the hydrogel matrix in order to provide a desired delivery profile.

The polyurethane hydrogel of the delivery device of the present invention in use may be in a swollen or "wet" state or unswollen in a "dry" or "desiccated" state as hereinbefore described. For example, in swollen state water content may be 30-40% by weight. Preferably, 25% by weight or less. More preferably, 5-10% by weight. Alternatively, in unswollen or dry state the polyurethane hydrogel usually contains little or no water. For example, about 1-2 wt %. Preferably, the water content of the hydrogel is about or less than 1%. More preferably, the water content is around 0.5% to around 0.8%. Even more preferably the water content of the polyurethane hydrogel is about or less than 0.1%.

Advantageously, the delivery device of the present invention in its "dry" state lends to easier storage before use, including at temperatures above 4° C., such as room temperature of 20° C., without loss of or reduced synthetic prostaglandin $PGE_1$ analogue activity. Indeed, as hereinbefore described, the synthetic prostaglandin $PGE_1$ analogue displays increased stability when formulated in the polyurethane hydrogel delivery devices of the present invention. Typically, said dry state may contain a water content of around 0.5% to around 0.8% and be stored with a desiccant to further reduce the water content of the delivery device.

Typically, the water content of the hydrogel is less than or about 0.1% when said hydrogel is desiccated or in "dry" state. Generally, the desiccated hydrogel may absorb water from the surroundings after administration.

Typically, the delivery device of the present invention comprises: synthetic prostaglandin $PGE_1$ analogue in a dose of about 25 to 400 micrograms (μg); has a thickness of around 0.4 to 1.5 mm; and has a weight of around 120 to 500 milligrams (mg). Typically, a dose of synthetic prostaglandin $PGE_1$ analogue of around 100 μg is contained within a polyurethane hydrogel of around 241 mg weight and of around 0.8 mm thickness.

In a further aspect of the present invention there is provided a method of preparing the pharmaceutical delivery device of the present invention, comprising the steps of:

a) contacting a polyurethane hydrogel with an aqueous solution of synthetic prostaglandin $PGE_1$ analogue such as to swell the hydrogel;

b) removing the swollen hydrogel from the solution; and c) drying the hydrogel to a desired water content.

In a yet further aspect of the present invention there is provided use of the pharmaceutical delivery device of the present invention for controlled administration of a synthetic prostaglandin $PGE_1$ analogue to a human or animal.

Embodiments of the present invention will now be described by way of figures and examples as follows:

FIGURES

FIG. 1—shows a graph displaying the results of enhanced stability of polyurethane hydrogel containing 100 μg misoprostol (desiccated and undesiccated batches) at 25° C. The results are compared against the stability of Misoprostol Oil standard (in the absence of polyurethane hydrogel) which degrades with time at 25° C.

Figure 2:
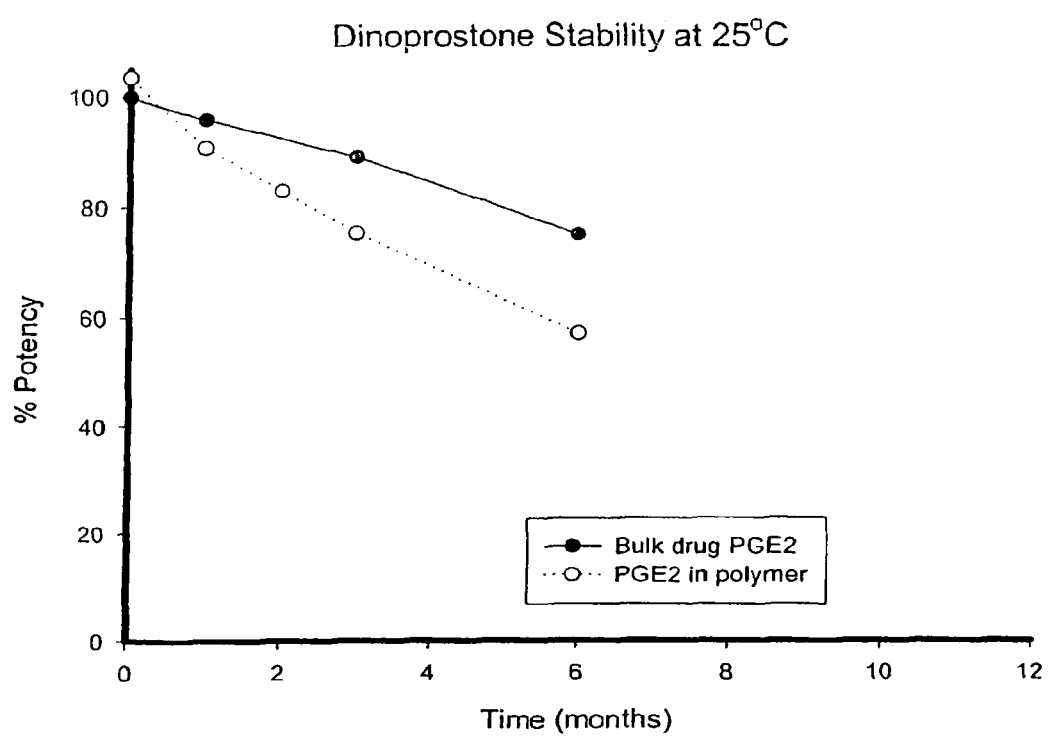

FIG. 2 (Comparison)—shows a graph of the stability of bulk drug crystal of dinoprostone (a $PGE_2$ prostaglandin), and dinoprostone loaded into polyurethane hydrogel at 25° C. The dinoprostone is less stable when contained in the hydrogel; and both the hydrogel and non-hydrogel samples show considerable degradation over time.

METHODS

The methods and results presented herein refer generally to pessaries, which are polyurethane hydrogels (as described previously in GB 2047093 and GB 2047094, and WO 2004/029125) loaded with varying amounts of misoprostol, as described.

1.1 Loading protocol for Misoprostol Inserts Purification 0.8 mm Polymer slices are purified by submerging in an excess of water for a first and second wash for a number of hours. The water is decanted after each wash and then the units are finally washed in an ethanol (25%):water mixture for a further few hours. This solution is again discarded.

Loading

The correct amount of misoprostol is weighed to achieve the desired final potency and dissolved in ethanol (25%):water along with the Butylated Hydroxy Anisole (BHA) used to stabilise the polymer. Sufficient of this solution is made to submerge the previously washed units and the units left to rotate in a closed vessel for a period at 4° C. The excess loading solution is decanted off and the units shaken dry.

Drying

Loaded inserts are placed in a tablet coating pan and rotated at ambient temperature and air and finally dehumidified air. Units may then be inserted into a retrieval tape and packaged appropriately. The solvent remaining in the units (water) is typically less than 1% at this stage (about 0.5-0.8%). The addition of a desiccated label inside the packaging reduces this down to 0.1-0.2%.

1.2 Measuring Misoprostol Potency Degradation Product/Impurity and BRA Content

The desiccated batches were packaged in preformed foil sachets containing desiccant labels.

Samples were taken at random from the batch. A minimum of 20 inserts were used for full testing.

100-400 μg Doses

10 Pessaries

HPLC Apparatus (ultraviolet absorbance detector at 280 nm with 6 mm pathlength)

Waring Blender with Stainless Steel Mini-Cup (110 ml) and Cap

Mobile Phase

Post Column Derivatising Agent

Mechanical Flask Shaker

BHA Misoprostol Standard Solution Preparation

The series of concentrations required for misoprostol standard preparation is described below. However, prior to the dilution to the mark of the misoprostol standard, pipette a volume of BHA stock solutions ca 40 μg/ml and 70 μg/ml prepared in mobile phase that would represent 10% of the total volume of the flask, i.e., 20 ml in 200 ml and 50 ml in 500 ml for respective extraction volume scenarios.

Misoprostol Standard Solution Preparation

A level one standard of approximately 8 mg and a level two standard of approximately 12 mg of misoprostol reference standard was accurately weighed and added each to separate 100 ml volumetric flask containing approximately 50 ml of 70% methanol mobile phase. Flasks were placed in an ultrasonic bath for 5 minutes and agitated on a flat bed shaker for no less than one hour. Standard flasks were diluted to volume with 70% methanol mobile phase. Depending on the target potency of the particular batch, the two standard solutions were diluted with 70% mobile phase using the guidelines outlined in table 1 below.

TABLE 1

Standard Dilution Guidelines for Misoprostol Analysis

| Batch Target Potency (μg/unit) | Standard Dilution Potency Determination |
|---|---|
| 100 | 1 in 20 |
| 200 | 1 in 10 |
| 300 | 1 in 15 |
| 400 | 1 in 10 |

Sample Preparation—for 100-400 μg Doses 10 pessary units were swollen in 40 ml of mobile phase. The units were then transferred to a Waring blender, macerated and quantitatively transferred to the appropriate volumetric flask through washing with mobile phase. The beaker used to swell the units was washed with mobile phase into the volumetric flask (see table 2). The flask and its contents were then shaken on a flat bed shaker for 2 hours, after 1 hour the neck of the flask was washed down with mobile phase. The flask was then diluted to the mark with mobile phase and contents allowed to settle and equilibrate for 20 minutes prior to sampling into HPLC vials.

TABLE 2

Extracting Volumes for Misoprostol Analysis

| Batch Target Potency (μg/unit) | Extraction Volume (ml) |
|---|---|
| 100 | 200 |
| 200 | 200 |
| 300 | 500 |
| 400 | 500 |

Misoprostol potency, together with the related impurities 8-iso misoprostol, dehydroxy misoprostol type A and unidentified impurity peaks were quantified with reference to the area response factor from the prepared misoprostol standard solutions using the following expression.
Note Standard Concentrations for Calibration are Expressed in Terms of μg Misoprostol Per ml Misoprostol/Impurity Content =

$$\frac{\text{Area Sample Peak}}{\text{Mean Misoprostol Standard } RF} \times \frac{\text{Sample Volume}}{\text{No. of Samples}}$$

$$BHA \text{ Content} = \frac{\text{Area Sample Peak}}{\text{Mean Standard } BHARF} \times \frac{\text{Sample Volume}}{\text{No. of Samples}}$$

Misoprostol potencies and degradation product contents are expressed as % label (for the batch dose) and % initial. % Initial relates the misoprostol potency at whatever test point to the initial potency determined.

EXAMPLES

Example 1

Stability Study of Misoprostol Oil at 25° C.

Misoprostol stability was tested over a period of 6 months. The misoprostol tested was the commercially available misoprostol in the form of an oil. Misoprostol was stored at a temperature of 25° C., and misoprostol content measured using HPLC at 0, 2, 4, 8 weeks and 3 and 6 months.

Results are shown below in Table 3:

TABLE 1

| Attribute | Specification | 0 | 2 w | 4 w | 8 w | 3 m | 6 m |
|---|---|---|---|---|---|---|---|
| Physical form | Clear colourless to yellow oil | Colourless oil | Colourless oil | Colourless oil | Clear colourless oil | Straw yellow oil | Yellow oil |
| Misoprostol content | 97.0-102.0% w/w | 101.59 | 99.61 | 98.59 | 96.87 | 93.63 | 57.07 |

Example 2

Stability Study of Desiccated and Undesiccated Polyurethane Polymers loaded with Misoprostol (Misoprostol Batches of Dose 100 μg, 200 μg, and 400 μg)

A stability study was carried out on batches of dose 100 μg, 200 μg, and 400 μg of misoprostol. Desiccated and undesiccated packaged pessaries were stored at −20° C., 4° C., 25° C. and 40° C./75% relative humidity, to study the effect of these conditions on the formulation over a 12 month period.

The main focus of the study was misoprostol potency and levels of degradation products/impurities. BHA levels, release rate testing, loss on drying and % swelling testing were also carried out. Results are shown below for desiccated and undesiccated misoprostol containing hydrogels stored at 25° C.

2.1-25° C. Data for Undesiccated Batches 2.1.1 100 μg Misoprostol Dose Batch

Shown in Table 4 are the misoprostol potencies and the levels of degradation product/impurities found for the undesiccated 100 μg batch, over 12 months at 25° C. Results are also displayed in FIG. 1.

TABLE 4

Misoprostol potency degradation product/impurities levels of undesiccated 100 μg batch, over 12 months at 25° C.

| | Misoprostol | | | 8-iso misoprostol | Misoprostol A |
|---|---|---|---|---|---|
| Time Point | μg/unit | % Label | % Initial | % Label | % Label |
| Initial | 103.9 | 103.9 | 100.0 | 0.7 | 0.1 |
| 4 weeks | 102.1 | 102.1 | 98.3 | 0.9 | 0.3 |
| 4 months | 98.8 | 98.8 | 95.1 | 1.0 | 0.5 |
| 7 months | 94.0 | 94.0 | 90.5 | 0.8 | 1.4 |
| 12 months | 97.9 | 97.9 | 94.2 | 1.0 | 2.5 |

Misoprostol potency for this batch falls over the 12 month duration of the study at 25° C. The potency value has dropped to 94.2% of the initial value. Levels of 8-iso misoprostol, over the study period at 25° C. reach a maximum of 1.0% label. Misoprostol A levels increase over the 12 month period, reaching a maximum of 2.5% label.

2.1.2 200 μg Dose Batch

Shown in Table 5 are the misoprostol potencies and the levels of degradation product/impurities found for the undesiccated 200 μg batch, over 12 months at 25° C.

TABLE 5

Misoprostol potency degradation product/impurities levels of undesiccated 200 μg batch, over 12 months at 25° C.

| | Misoprostol | | | 8-iso misoprostol | Misoprostol A |
|---|---|---|---|---|---|
| Time Point | μg/unit | % Label | % Initial | % Label | % Label |
| Initial | 206.3 | 103.1 | 100.0 | 0.5 | ND |
| 4 months | 202.3 | 101.2 | 98.1 | 0.9 | 0.8 |
| 12 months | 192.8 | 96.4 | 93.5 | 1.1 | 1.5 |

ND—none detected

Misoprostol potency has fallen for this batch over the 12 month duration of the study at 25° C. The potency value has dropped to 93.5% of the initial value. Levels of 8-iso misoprostol reached 1.1% label. Misoprostol A levels increase over the 12 month period, reaching a maximum of 1.5% label.

2.1.3 400 μg Dose Batch

Shown in Table 6 are the misoprostol potencies and the levels of degradation product/impurities found for the undesiccated 400 μg batch, over 12 months at 25° C.

TABLE 6

Misoprostol potency degradation product/impurities levels of undesiccated 400 μg batch, over 12 months at 25° C.

| Time Point | Misoprostol | | | 8-iso misoprostol | Misoprostol A |
|---|---|---|---|---|---|
| | μg/unit | % Label | % Initial | % Label | % Label |
| Initial | 424.3 | 106.1 | 100.0 | 1.0 | 0.5 |
| 4 weeks | 416.6 | 104.2 | 98.2 | 1.0 | 0.8 |
| 4 months | 404.7 | 101.2 | 95.4 | 1.1 | 1.2 |
| 7 months | 389.2 | 97.3 | 91.7 | 1.0 | 1.8 |
| 12 months | 382.1 | 95.5 | 90.1 | 1.3 | 2.6 |

Misoprostol potency has dropped for this batch over the 12-month duration of the study at 25° C. The potency value has dropped to 90.1% of the initial value. Levels of 8-iso misoprostol reached 1.3% label. Misoprostol A levels increase over the 12-month period, reaching a maximum of 2.6% label.

2.1.4 100 μg-400 μg Doses—Summary of Findings for Undesiccated Doses—Storage at 25° C.

Misoprostol potency in all three undesiccated doses falls over the 12-month duration of the study at 25° C. Potency values have dropped to between 90.1% and 94.2% of the initial values of the doses. 400 μg batch, shows the largest drop to 90.1% initial. Levels of 8-iso misoprostol do not show any marked change over the study period at 25° C. with maximums of 1.3% label found. Misoprostol A levels increase over the 12-month period, reaching maximum levels of 2.6% label in the 400 μg batch, at 25° C.

2.2-25° C. Data for Desiccated Batches 2.2.1 100 μg Dose Batch

Shown in Table 7 are the misoprostol potencies and the levels of degradation product/impurities found for the desiccated 100 μg batch, over 12 months at 25° C. Results are also displayed in FIG. 1.

TABLE 7

Misoprostol potency degradation product/impurities levels of desiccated 100 μg batch, over 12 months at 25° C.

| Time Point | Misoprostol | | | 8-iso misoprostol | Misoprostol A |
|---|---|---|---|---|---|
| | μg/unit | % Label | % Initial | % Label | % Label |
| Initial | 103.9 | 103.9 | 100.0 | 0.7 | 0.1 |
| 4 weeks | 90.1 | 90.1 | 86.7 | 0.2 | 0.4 |
| 6 months | 101.6 | 101.6 | 97.8 | 0.5 | 1.4 |
| 12 months | 102.4 | 102.4 | 98.6 | 0.7 | 1.9 |

Generally for this dose misoprostol potencies fall within 97% to 100% initial over the 12 month duration of the study at 25° C. The exception is the 3-month time point. At this test point the misoprostol potency was found to be 86.7% of the initial value. This is out of character with the other test points at this temperature for this batch and of other batches tested at this test point for the same storage condition. For levels of 8-iso misoprostol, no change over the study period at 25° C. with maximums of 0.7% label found. Misoprostol A levels increase slightly over the 12-month period, reaching maximum levels of 1.9% label.

2.2.2 200 μg Dose Batch

Shown in Table 8 are the misoprostol potencies and the levels of degradation product/impurities found for the desiccated 200 μg batch, over 12 months at 25° C.

TABLE 8

Misoprostol potency degradation product/impurities levels of desiccated 200 μg batch, over 12 months at 25° C.

| Time Point | Misoprostol | | | 8-iso misoprostol | Misoprostol A |
|---|---|---|---|---|---|
| | μg/unit | % Label | % Initial | % Label | % Label |
| Initial | 209.2 | 104.6 | 100.0 | 1.0 | 0.6 |
| 12 months | 202.0 | 101.0 | 96.6 | 1.1 | 2.6 |

Misoprostol potency drops very slightly over the 12 month duration of the study at 25° C. for this dose, down to 96.6% initial. Levels of 8-iso misoprostol show no change over the study period at 25° C. with maximums of 1.1% label found. Misoprostol A levels increase slightly over the 12-month period, reaching maximum levels of 2.6% label.

2.2.3 400 μg Dose Batch

Shown in Table 9 are the misoprostol potencies and the levels of degradation product/impurities found for the desiccated 400 μg batch, over 12 months at 25° C.

TABLE 9

Misoprostol potency degradation product/impurities levels of desiccated 400 μg batch, over 12 months at 25° C.

| Time Point | Misoprostol | | | 8-iso misoprostol | Misoprostol A |
|---|---|---|---|---|---|
| | μg/unit | % Label | % Initial | % Label | % Label |
| Initial | 424.3 | 414.0 | 100.0 | 1.0 | 0.5 |
| 4 weeks | 424.4 | 106.1 | 100.0 | 1.0 | 0.8 |
| 6 months | 409.1 | 102.3 | 96.4 | 1.6 | 1.2 |
| 12 months | 408.3 | 102.1 | 96.2 | 0.8 | 2.2 |

Misoprostol potency drops very slightly over the 12-month duration of the study at 25° C. for this dose, down to 96.2% initial. Levels of 8-iso misoprostol show no change over the study period at 25° C. although a maximum of 1.6% label is found at 6 months. Misoprostol A levels increase slightly over the 12-month period, reaching maximum levels of 2.2% label 2.2.4 100 μg-400 μg Doses—Summary of Findings for Desiccated Doses—Storage at 25° C.

For all three desiccated doses, misoprostol potency drops very slightly over the 12-month duration of the study at 25° C. Generally potencies fall within 96% to 100% of the initial values. The exception being the 100 μg batch after 4 weeks, which has a potency of 86.7% of the initial value. This is out of character with the other test points at this temperature for this batch. Levels of 8-iso misoprostol showed no change over the study period at 25° C. although a maximum of 1.6% label is found. Misoprostol A levels increase slightly over the 12 month period, reaching maximum levels of 2.6% label in the 200 μg batch, at 25° C.

2.3 Summary of Results for Both Desiccated and Undesiccated Misoprostol-Containing Hydrogels Misoprostol potency and levels of degradation products/impurities remain unchanged after 12 months/15 months storage at −20° C. for both desiccated and undesiccated doses.

Desiccation appears to improve the stability of the misoprostol over 12 months at 4° C. and particularly at 25° C. and 40° C. At 25° C., after 12 months, desiccated batches have misoprostol potencies greater than 95% of their initial values, whereas undesiccated batches of the same dose have potencies ranging from 90% to 94% of their initial value. At 40° C., after 12 months desiccated doses have misoprostol potencies of typically 90% of their initial values, whereas undesiccated doses range from 83% to 88% of their initial values. Correspondingly, at 40° C. levels of misoprostol A are greater in undesiccated batches than desiccated batches of the same dose.

Generally misoprostol A is the main degradation product. 8-iso misoprostol stability remained relatively unchanged (results not shown).

Levels of the polymer stabilising excipient, butylated hydroxy anisole (BHA) remain fairly constant in all desiccated and undesiccated batches at 25° C. over 12 months.

Generally it was found that the misoprostol release data did not change over 12 months at conditions tested for either desiccated or undesiccated batches of the three doses (results not shown).

Loss on drying data shows no change over 12 months at 25° C. for undesiccated batches (results not shown). There was a decrease in loss on drying values for desiccated batches at 25° C. (results not shown).

% Swelling values remained within specification (275-3250) for all the desiccated doses at 25° C. over the 12-month study period (results not shown).

Use of desiccation enhances the stability of the misoprostol formulation.

Example 3

Comparative Stability Results at 25° C. For Polyurethane Hydrogel Loaded with Dinoprostone The following Table 10 shows the stability of dinoprostone (a $PGE_2$ prostaglandin) both as a bulk drug crystal and contained within a polyurethane hydrogel matrix at 25° C. Measurements are taken at 0, 1, 2, 3, and 6 months. The following results are for comparative purposes only and are not intended to form part of the present invention.
[See also R. G. Stehle, 1982, Methods in Enzymology, Vol. 86, pp 436-458]

TABLE 10

| Test Point (months) | Dinoprostone (% potency) | Dinoprostone in the hydrogel (% potency) |
|---|---|---|
| 0 | 100 | 103.5 |
| 1 | 96 | 90.9 |
| 2 |  | 83.0 |
| 3 | 89 | 75.3 |
| 6 | 75 | 57.1 |

The above results are also depicted in FIG. 2.

The stability of the dinoprostone contained in the hydrogel is decreased compared with the dinoprostone bulk drug itself.

Thus, in contrast to the misoprostol hydrogel formulation of the present invention, the formulation of dinoprostone in a hydrogel reduces its storage stability. Moreover, dinoprostone both with and without hydrogel shows marked degradation on storage.

The invention claimed is:

1. A pharmaceutical delivery device, comprising:
a formulation comprising misoprostol in a polyurethane hydrogel, wherein the hydrogel has a water content of less than 0.2% by weight.

2. The delivery device of claim 1, wherein the polyurethane hydrogel is a cross-linked hydrogel.

3. The delivery device of claim 2, wherein the cross-linked hydrogel is the reaction product of a polyethylene glycol, a triol and a diisocyanate.

4. The delivery device of claim 3, wherein the polyethylene glycol has a molecular weight ranging between 4000 and 35,000.

5. The delivery device of claim 4, wherein the polyethylene glycol has a molecular weight ranging between 4000 and 8000.

6. The delivery device of claim 3, wherein the polyethylene glycol is selected from the group consisting of PEG2000, PEG4000, PEG6000 and PEG8000.

7. The delivery device of claim 3, wherein the triol is hexanetriol.

8. The delivery device of claim 3, wherein the diisocyanate is selected from the group consisting of dicyclohexylmethane diisocyanate, dicyclohexylmethane-4,4-diisocyanate, diphenylmethane-4,4-diisocyanate, and 1,6-hexamethylene diisocyanate.

9. The delivery device of claim 1, wherein the polyurethane hydrogel is a linear hydrogel.

10. The delivery device of claim 1, wherein the misoprostol is present in the formulation in an amount ranging between 25 and 400 μg.

11. The delivery device of claim 10, wherein the misoprostol is present in the formulation in an amount of 100 μg.

12. The delivery device of claim 10, wherein the misoprostol is present in the formulation in an amount of 200 μg.

13. The delivery device of claim 1, wherein the hydrogel has a water content of less than 0.1% by weight.

14. The delivery device of claim 1, wherein the hydrogel has a water content in the range of 0.1% to 0.2% by weight.

15. The delivery device of claim 1, further comprising butylated hydroxyl anisole.

16. The delivery device of claim 1, wherein the device is selected from the group consisting of a suppository, a vaginal pessary, a buccal insert and an implant.

17. A method for inducing labor, comprising:
contacting the delivery device of claim 1 with a body cavity.

18. The method of claim 17, wherein the delivery device is a vaginal pessary.

19. An article, comprising:
the pharmaceutical delivery device of claim 1, and a desiccant.

20. The delivery device of claim 1, wherein the misoprostol is present in the formulation in an amount ranging between 100 and 400 μg.

21. The delivery device of claim 1, wherein the misoprostol is present in the formulation in an amount ranging between 100 and 200 μg.

* * * * *

UNITED STATES PATENT AND TRADEMARK OFFICE
CERTIFICATE OF CORRECTION

PATENT NO. : 8,709,482 B2
APPLICATION NO. : 13/906905
DATED : April 29, 2014
INVENTOR(S) : Steven Robertson It is certified that error appears in the above-identified patent and that said Letters Patent is hereby corrected as shown below:

Title Page, Column 1, under Related U.S. Application Data, line 19 approximately and below "8,491,934", please insert:

item -- (30) Foreign Application Priority Data
      Aug. 05, 2004   (GB) .................... 0417401.7 --

Title Page 4, Column 2, under OTHER PUBLICATIONS, line 7, delete "diethylel" and insert therefor: -- diethylene --

In the Specification

Column 7, line 65, delete "BRA" and insert therefor:
-- BHA --

Column 12, line 42, delete "label" and insert therefor:
-- label. --

Column 13, line 22 approximately, delete "3250" and insert therefor:
-- 325% --

Signed and Sealed this
Twenty-first Day of October, 2014

Michelle K. Lee
*Deputy Director of the United States Patent and Trademark Office*